US012569156B2

(12) United States Patent
Risman

(10) Patent No.: US 12,569,156 B2
(45) Date of Patent: Mar. 10, 2026

(54) DEVICE FOR MICROWAVE FIELD DETECTION

(71) Applicant: Scanwaves AB, Torsby (SE)

(72) Inventor: Per Olov Risman, Härryda (SE)

(73) Assignee: Scanwaves AB, Torsby (SE)

( * ) Notice: Subject to any disclaimer, the term of this patent is extended or adjusted under 35 U.S.C. 154(b) by 355 days.

(21) Appl. No.: 18/252,841

(22) PCT Filed: Nov. 11, 2021

(86) PCT No.: PCT/EP2021/081402
§ 371 (c)(1),
(2) Date: May 12, 2023

(87) PCT Pub. No.: WO2022/101350
PCT Pub. Date: May 19, 2022

(65) Prior Publication Data
US 2024/0008758 A1    Jan. 11, 2024

(30) Foreign Application Priority Data
Nov. 13, 2020    (SE) .................................... 2051329-7

(51) Int. Cl.
*A61B 5/0507* (2021.01)

(52) U.S. Cl.
CPC .... *A61B 5/0507* (2013.01); *A61B 2562/0228* (2013.01)

(58) Field of Classification Search
CPC ...................... A61B 2562/0228; A61B 5/0507
See application file for complete search history.

(56) References Cited

U.S. PATENT DOCUMENTS

| | | | | |
|---|---|---|---|---|
| 4,392,039 | A | 7/1983 | Risman | |
| 5,470,352 | A * | 11/1995 | Rappaport | A61B 18/18 607/101 |
| 6,330,259 | B1 * | 12/2001 | Dahm | H01S 3/0941 372/75 |
| 2023/0007851 | A1 * | 1/2023 | Hancock | A61B 18/1815 |

FOREIGN PATENT DOCUMENTS

| | | |
|---|---|---|
| CN | 104698231 B | 10/2018 |
| EP | 3373808 B1 | 5/2020 |
| JP | 2007278820 A | 10/2007 |

(Continued)

OTHER PUBLICATIONS

Swedish Search Report for Patent Application No. 2051329-7, mailed on Jul. 12, 2021, 3 pages.

(Continued)

*Primary Examiner* — Gerald Johnson
(74) *Attorney, Agent, or Firm* — Brake Hughes Bellermann LLP

(57) ABSTRACT

An electromagnetic receiving device configured to discriminately react predominantly to an external electric field directed along an axis of said device, comprising a high-permittivity dielectric rod as receiving element, wherein said dielectric rod is oriented along said axis and has a receiving end to be directed towards an object under study, and wherein the device is configured to be essentially resonant with a circularly cylindrical TM00 mode.

11 Claims, 2 Drawing Sheets

(56)            References Cited

FOREIGN PATENT DOCUMENTS

JP           2013044660 A     3/2013

OTHER PUBLICATIONS

Y. Cheng, et al., "Dielectric Properties for Non-Invasive Detection of Normal, Benign, and Malignant Breast Tissues Using Microwave Theories", Thoracic Cancer 9; ISSN 1759-7706, 2018, pp. 459-465.
A. Mobashsher, et al., "Microwave System to Detect Traumatic Brain Injuries Using Compact Unidirectional Antenna and Wideband Transceiver With Verification on Realistic Head Phantom", IEEE Transactions on Microwave Theory and Techniques, vol. 62, No. 9, Sep. 2014, pp. 1826-1836.
N. Petrovic, et al., "Antenna Applicator Design for Microwave Imaging of the Interior of Human Breasts", Journal of Physics D: Applied Physics, Institute of Physics Publishing Ltd., GB, vol. 47, No. 38, Aug. 28, 2014, 10 pages.
M. Gastine, et al., "Eletromagnetic Resonances of Free Dielectric Spheres", IEEE Transactions on Microwave Theory and Techniques, vol. MTT-15, No. 12, Dec. 1967, pp. 694-700.
International Search Report and Written Opinion for PCT Application No. PCT/EP2021/081402, mailed on Mar. 3, 2022, 11 pages.
Risman, P.O. et al.: "A Study of SAR Values in Induction, High Frequency and Microwave Nearfields," 2020 23rd International Microwave and Radar Conference (Mikon), 2020, pp. 386-391.

* cited by examiner

DEVICE FOR MICROWAVE FIELD DETECTION

CROSS REFERENCE TO RELATED APPLICATIONS

This application is a 35 U.S.C. § 371 National Phase Entry Application from PCT Application No. PCT/EP2021/081402, filed on Nov. 11, 2021, entitled "DEVICE FOR MICROWAVE FIELD DETECTION", and designating the U.S., which in turn claims priority to SE Application No. 2051329-7, filed on Nov. 13, 2020, the disclosures of which are incorporated by reference herein in their entireties.

FIELD OF THE INVENTION

The present invention relates to quantification of inhomogeneities in objects by means of electromagnetic fields. In particular, the present invention relates to detection of dielectric irregularities (deviations of electromagnetic properties) inside an object under study (OUS). Embodiments of the invention are suitable for investigations of tissue-internal irregularities caused by, for example, tumors, necroses, hemorrhages or ruptures in human breasts, heads or limbs. Other embodiments may be suitable for other medical, veterinary or industrial applications.

TECHNICAL BACKGROUND

It is generally desirable that receiving devices of the kind used for the above purpose are selectively sensitive primarily to the electric nearfield emission with a direction straight out from the surface of the OUS. The reason for this is that a transmitting applicator, for example of the kind described in EP 3 373 808 B1, may behave as half of an emitting magnetic dipole, thus essentially inducing a circumferential electric field in a homogeneous OUS. An internal dielectric irregularity in the object will then, by diffraction, create an electric field with other directions than the primary induced electric field.

A number of electric field sensing devices are described in the above-mentioned EP 3 373 808 B1, to which reference is made. However, only receiving devices having geometry and fields as described in relation to FIGS. 3, 4, and 5 of that patent have the desired property of selectively sensing the axially directed electric field. That prior art device basically relies on a resonant circular $TM_{01p}$ type mode created in and bound to a high-permittivity partially metallized ceramic body. Even if that device can function satisfactorily for some applications, it suffers to some extent from a tendency to not only sense the centered axial electric nearfield but also nearfields of the circular $TM_{11}$ type, particularly when designed for operating frequencies in the region 2 to 4 GHz. In addition, the device design is rather complex and expensive to manufacture.

SUMMARY OF THE INVENTION

There is therefore a need for a receiving device that does not have the above-mentioned field reception drawback, and that can operate at higher frequencies than the possibly preferred 0.5 to 2 GHz for the aforementioned transmitting device. There is also a general need for a device that is easier to manufacture.

Picking up the diffracted surface-perpendicular E field signal from an inhomogeneity should typically employ a directly contacting device (i.e. a device intended to be brought into direct contact with the outer surface of the OUS) having a higher permittivity of its main sensing part than that of its contacting OUS part. If a short axial air distance is used between this receiving part and the surface of the OUS, there will be an amplification of this electric field component, due to the displacement (D) vector continuity in this case. However, the energy content in this highly evanescent surface-perpendicular E component will be much smaller than when the device end is in direct contact with the object. The component will also be largely unchanged if the real permittivity of the object does not deviate by more than a factor of about two from that of the directly contacting part of the receiving device.

However, in some embodiments of the present invention, it is preferred that the permittivity of the device is slightly higher than that of the object, for reducing the sensing area, due to the resonant design of the rod-shaped sensing device, and creating a better stability of the resonant field properties of the device under variations of the object permittivity.

A generally desired property of a sensor or receiving device for picking up the surface-perpendicular E field is that it should be significantly less sensitive to the surface-parallel E field than to the surface-perpendicular E field. This can be accomplished by filtering-out the surface-parallel E component by employing a mode in the sensor body that favors the perpendicular E component, and/or by the residual radially directed E fields of the sensor mode being circumferentially equal and thus directed away from the axis of the rod-shaped device. Due to the small rod diameter in relation to the wavelengths at the OUS surface caused by internal diffraction effects and also by the primarily induced surface-parallel E field in the OUS, these components are either very weak at the rod position by a standing wave minimum of the external surface-parallel E field (due to the magnetic wall effect), or this has a unidirectional surface-parallel direction in the rod sensor region. As seen in FIG. 2, this field will influence the sensor in opposite ways on all diametrical sides thereof since the sensor fields are rotationally symmetrical. This results in no reception of the overall surface-directed E field. This phenomenon becomes stronger with a higher-permittivity rod, since such a rod will have a sufficiently small diameter and also be sufficiently resonant due to its higher permittivity than that of the contacting OUS.

A receiving device according to the present invention uses the particular properties of the circularly cylindrical $TM_{00}$ mode with axial index p near zero. This lowest resonant mode in a free rod-shaped dielectric is known per se and its two-dimensional properties can be calculated by analytical Bessel functions, for example under conditions of an impinging free-space plane wave with its E field parallel to the axis of a long rod. It can also be analytically calculated by using a complex frequency concept, i.e. power generation in the whole space under study.

It is known that a particular resonance can occur with a rod having such a high ε' that the effect becomes significant. In addition, its ε' must typically be at least as high as that of the contacting part of the OUS, and biological materials have a significant water content (water has ε' larger than 70). These factors result in a need for a rod ε' of at least 20. This resonance is labelled $TM_{00}$ since there are neither any circumferential (first index) nor radial (second index) field variations in the rod. The electric field is axial and the external magnetic field is circumferential. When energized, there will be a displacement $(\partial D/\partial t)$ current in the rod. This current will be linked to an encircling H field around the rod, and these fields may then be 90 degrees out of phase with each other. An interesting condition for this, which is also the resonant condition where the oscillating energies are equal, is when the desirable coupling phenomena are the strongest.

The assumption in the two-dimensional case is now that the E field is equal over the rod cross section and insignificant outside the rod, and that the magnetic energy contribution further away from the rod axis than $\frac{1}{2}\lambda_0$ can be disregarded. Then, a transcendental equation can be set up by equating the oscillating electric and magnetic energies. A numerical formula derived from this solution for different lossless rod permittivities $\varepsilon'$ gives the resonant rod diameter $D_{res}$ in millimeters at the free space wavelength $\lambda_0$ in millimeters as $$D_{res}=\lambda_0\cdot 0.335\cdot\exp[-0.589\ \ln(\varepsilon')]$$

For 3 GHz ($\lambda_0=100$ mm) and $\varepsilon'=70$ the formula gives $D_{res}\approx 2.75$ mm.

In practice, where there is a need for an assembly including dielectric materials surrounding the rod, there may be a significant E field energy outside the rod. Experimental methods are then still conveniently used for obtaining the desired resonant frequency. Variations in the tabulated or pre-measured $\varepsilon'$ of the rod should also be considered.

The two basic criteria—filtering-out the OUS surface-parallel E component by employing a mode in the sensor body that favors the perpendicular E component, and/or the surface-parallel E fields of the sensor mode being radial—are both fulfilled by the $TM_{00}$ sensor end field pattern when used in the transmitting mode as shown in FIG. 2, and the latter effect becomes more significant the smaller the sensor rod diameter is, i.e. for a higher $\varepsilon'$ of the sensor rod material.

Under the $TM_{00}$ resonant condition with long axial wavelength in the rod, the axial D (and by that E) field, will be 90° out-of-phase with the surrounding H and thus the B field caused by the $\partial D/\partial t$ displacement current in the rod. This D field will continue from the rod into the object, as seen in the reciprocal case of the device being used as source; this is illustrated in FIG. 2. However, the axial E field is continuous across the cylinder surface under plane-wave excitation ($E^{in}=E_{\varepsilon'}$) but the electric field energy content is much lower due to the high $\varepsilon'$ of the rod.

The case with an impinging plane wave source E field—such as by interfering external fields—being perpendicular to the rod axis will result in an extremely low coupling. The theoretical solution for this case is quasi-static and well-known: $E_{\varepsilon'}/E^{in}=2/(\varepsilon'+1)$. This means that the discrimination of reception of the two E field polarizations by the object-perpendicular rod will be very high and is thus a further reason for the choice of a receiving rod with high $\varepsilon'$. In embodiments of the present invention, the rod has an $\varepsilon'$ that is at least 20 is some applications with low water content OUS, and preferably in most cases at least 40. For practical reasons, it may not be useful to have an $\varepsilon'$ that is higher than about 100.

The signal extraction from the rod is in its opposite end, i.e. away from the OUS, by a coaxial line with the center conductor contacting a small central metal-filled hole in the rod end. The resonant action and the coupling factor are improved with a higher characteristic impedance of the coaxial line. The characteristic impedance of the coaxial line may, for example, be about 100Ω.

Due to such a high characteristic impedance of the coaxial line, it becomes favorable to use direct rectification by a schottky diode and simple DC low-pass filtering of the signal, rather than a transition to a standard coaxial line. The primary signal can then be amplified and AD-converted by a small built-in battery-operated device, which also operates a small wireless unit, e.g. a Bluetooth unit, for signal transmission, so that otherwise disturbing metallic cables can be avoided. This is possible since only the amplitude (and not also the phase) of the received signal is of interest, which significantly simplifies the overall system.

In another aspect, there is provided an apparatus for quantification of inhomogeneities in objects by means of electromagnetic fields, comprising one or more electromagnetic transmitting devices and one or more receiving devices. The apparatus is configured to collect diffracted signals from internal dielectric inhomogeneities in the OUS by using orthogonality relations between a primary magnetic field generated by the transmitting device, an electric field induced in the OUS by the primary magnetic field, and an electric field caused by diffraction by an internal dielectric inhomogeneity in the OUS. The apparatus may comprise means for direct readout of the received signals as a function of the receiving device position on the OUS, including means for computing, using the signals and device positions, a diffracted signal map over a large part of the surface of the OUS.

BRIEF DESCRIPTION OF THE DRAWINGS

In the detailed description below, reference will be made to the accompanying drawings, on which FIG. 1 schematically shows an electromagnetic receiving device according to the present invention.

DETAILED DESCRIPTION

Figure 1:
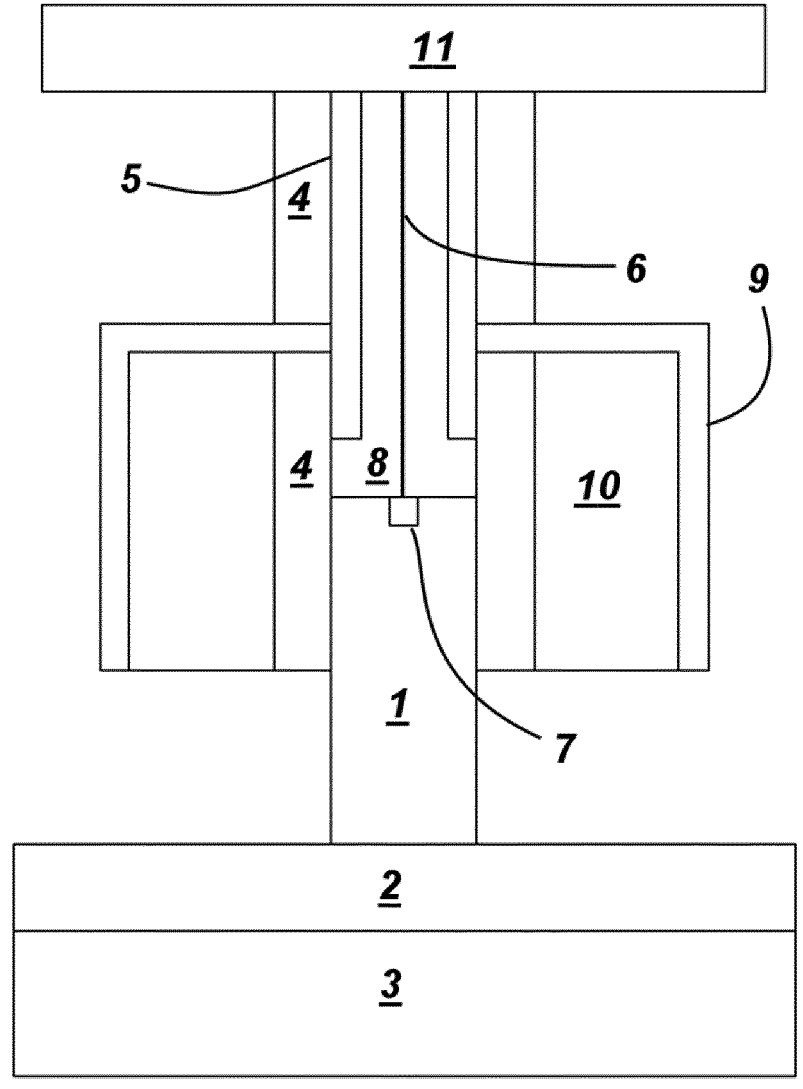

FIG. 1 schematically shows a cross section of a rotationally symmetric device according to a preferred embodiment of the invention, for 3 GHz operation. A rod 1 with permittivity $\varepsilon'=70$ is 9 mm long and has a diameter of 2.75 mm. The object under study (OUS) has a 2 mm thick skin layer 2, below which there is, in this example, breast fat 3. There is a protective holder 4 of a low-permittivity plastic, fitting the rod as well as the outside of the metallic outer coaxial conductor 5, having an inner diameter of about 2.5 mm or less. The inner 0.2 mm diameter coaxial conductor 6 is soldered to a 1.5 mm diameter metal filling 7 which is reliably in contact with the surrounding hole in the ceramic end of the rod opposite to the receiving end. One preferred way of obtaining good contact between the metal filling 7 and the surrounding hole is to use a lead-bismuth alloy, which has a slight expansion upon solidification due to the thermal properties of bismuth. There is an airgap 8 between the outer metal part 5 of the coaxial line and the rod 1, for obtaining the desired performance of the transition. The inner space above this is also air. Since there may be some unwanted external fields emanating from the OUS-contacting area, a metal holder 9 with a dielectric-filled quarterwave wavetrap may be affixed at the external coaxial conductor 5. Further, a compartment 11 for holding electronics such as a signal converter to DC, circuitry for wireless communication, etc. may also be provided.

Figure 2:
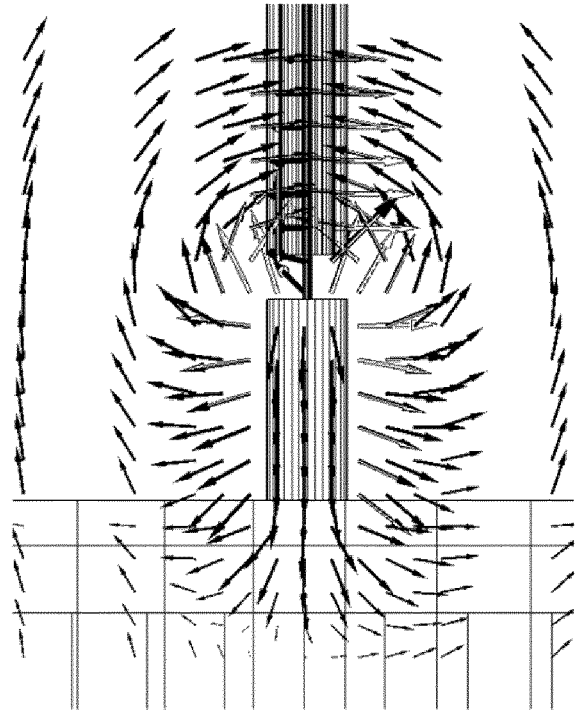
FIG. 2 illustrates the overall momentary E field as arrows in logarithmic scale in a vertical plane of the device axis, when used in transmission mode.

FIG. 2 shows the overall momentary E field as arrows in logarithmic scale in a vertical plane of the device axis, when used in transmission mode. In a transmitter-receiver system this performance will of course be reciprocal, and the above-mentioned external fields without the wavetrap are seen. The dominant axial E field at the receiving rod end is also seen.

Figure 3:
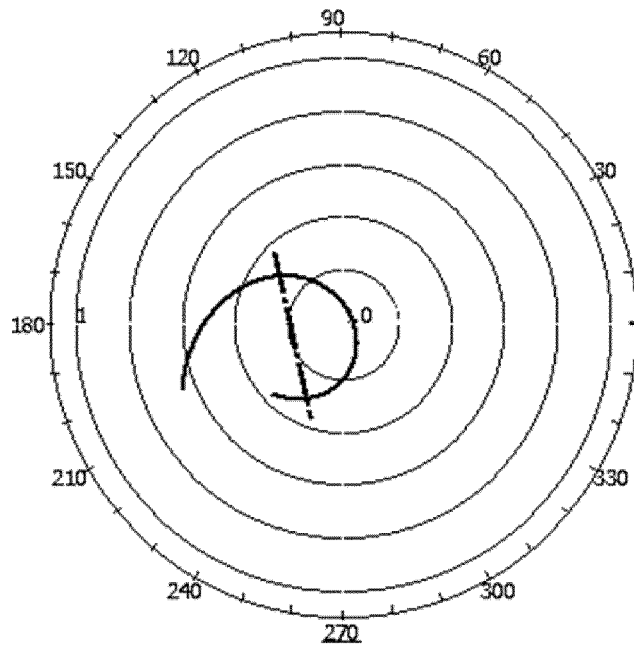
FIG. 3 is a graph showing the system reflection factor in conventional polar format.

FIG. 3 shows the system reflection factor as modelled with a coaxial input line having a characteristic impedance of 110Ω. The frequency span is from 2100 to 4000 MHz and the diametrical line across the circular part, used for determination of the loaded quality factor (Q value), has crosspoints at 2590 (closer to the left end in FIG. 3) and 3660 MHz, which correspond to a loaded Q value of 3.0 and an unloaded Q value thus being twice of that due to the matching at resonance, i.e. about 6. A low Q value is generally advantageous, but is needs to be sufficiently high in order to stabilize the $TM_{00}$ mode field pattern. Hence, in embodiments of the present invention, the loaded Q value is preferably 3 or higher, corresponding to an unloaded Q value of 6 or higher. In general, an inherent Q value of the rod material should preferably be much higher in order not to disturb the system resonance. The material selected for the rod may, for example, have a real permittivity ε' of and a corresponding loss factor ε'' such that ε'/ε'' exceeds about 50.

In the preferred embodiment, the rod is in direct contact with a surface of the OUS during use. This gives the best coupling of the axial E field across the boundary. There will of course be a lower E axial field intensity in the rod than in the OUS when ε' of the latter is lower than that of the rod, but in the case of e.g. a contacting thin skin layer with a lower-ε' tissue below, the evanescence of the incoming surface-perpendicular E field will in total not be weakened much, due to the continuity of the corresponding D vector. However, in cases where the OUS has an uneven surface in the sub-millimeter scale, an intermediate liquid layer may be applied, as in the comparable case with ultrasound examinations, and then for avoiding air pockets. A microwave-adapted liquid for this purpose should then have an ε' which is not much lower than about half that of the rod material, i.e. its ε' is to be at least about 20 in the preferred embodiment.

The rod length is per se not a sensitive parameter, but one should consider the need for the $TM_{00}$ mode with very low axial variation of the field to be established, and also the need for locating its top end transition part to the coaxial line sufficiently far away from the object contacting end, for avoiding the above-mentioned undesired emissions. There may also be a need for a free end region below the device holder 4, as shown in FIG. 1, for viewing of any marked contact spots on the OUS and also for cleaning purposes. A rod length of about 10 mm for 3 GHz operation may be sufficient under most conditions, with about half of this being covered by the holder 4.

As will be understood, there is a need for the coaxial outer conductor 5 to end some distance above the rod, in order for the creation of the $TM_{00}$ field in the latter not to be significantly disturbed. The length of the free center conductor 6 has also an influence on the coupling field impedance. It has been found that this gap 8 is suitably between 2 and 4 mm, at 3 GHz. There will then of course, in the preferred embodiment, be an emission of a nearfield into free space from this junction region, but since the free length is much shorter than a quarter wavelength, this does not deteriorate the performance significantly, since most of the field will be non-radiating. However, the wavetrap 9, 10 above will reduce any unwanted interfering emissions.

Typical embodiments will include a holder 4 as seen in FIG. 1. Such holder should preferably have a minimal influence on the overall performance and should thus generally be made from a low loss, low-ε' material. Typical suitable plastic materials have ε' less than about 3. With such a choice, the material thickness can be several mm.

The coaxial inner conductor 6 has a diameter of only 0.2 mm and is in air, in the preferred embodiment for 3 GHz. This corresponds to a characteristic impedance of 150Ω, which gives a coupling factor near 1 at resonance, as seen in FIG. 3. A thicker wire will provide undercoupling, with best coupling for slightly lower frequency. While the inner conductor is preferably protected from external influences, it does not need to be strained or tensed since a radial offset of the position does not influence its characteristic impedance much. In any case, its length does not need to be more than 20 mm and it is soldered at both ends.

The diameter and depth of the hole 7 with metal can be experimentally determined, for example, according to the design principle is discussed in U.S. Pat. No. 4,392,039. As shown in FIG. 3, critical coupling is achievable.

Signal Processing and Presentation

This section is provided for creating a complete picture of the system, with reference being made to the patent publication EP 3 373 808 B1 as background.

The coaxial line enters the compartment or box 11, which contains standard engineering sub-components such as for rectification, low-pass filtering, amplification, and then an output of a DC signal corresponding to the received averaged signal from the rod. This signal can be conveyed by a metallic cable to the system processing unit with DC feed to the amplifier in the cable, or a small battery can be used for energizing the internal subsystems. The box 11 may also include an ND converter and a Bluetooth or similar wireless transmitter.

In use, one or a few devices for field detection is/are moved over the OUS, for recording position-dependent signals. This means that positions of the devices should be combined with signal readings, for obtaining a kind of "signal map" over at least part of the object surface. It is also conceivable that several receiving devices are located in a predetermined geometric pattern over the surface of the OUS. If a transmitting device according to the previously referenced EP 3 373 808 B1 is used, also that device needs to have at least two different positions, due to the fact that there is no induced E field along its axis, thus not providing any diffraction signals from any dielectric irregularity in that region.

The invention claimed is:

1. An electromagnetic receiving device configured to discriminately react predominantly to an external electric field directed along an axis of the electromagnetic receiving device, comprising, as receiving element, a dielectric rod with permittivity ε' in a range between 20 and 100, wherein the dielectric rod is oriented along the axis and has a receiving end to be directed towards an object under study, and wherein the dielectric rod has a diameter and a permittivity resulting in an essentially resonant condition of a circularly cylindrical $TM_{00}$ mode, the electromagnetic receiving device further comprising a transition to a coaxial line in a rear end of the dielectric rod opposite to the receiving end, the coaxial line having an outer conductor separated by a gap to the dielectric rod and an inner conductor in direct contact with a metalized hole in a center of a circular end of the dielectric rod.

2. The electromagnetic receiving device of claim 1, wherein the permittivity of the dielectric rod is higher than an average permittivity of an outer 5 mm of the object under study, in a frequency range 1 to 5 GHz.

3. The electromagnetic receiving device of claim 2, wherein the dielectric rod has a loss factor $\varepsilon''$ such that $\varepsilon'/\varepsilon''$ exceeds about 50.

4. The electromagnetic receiving device of claim 1, in which a characteristic impedance of the coaxial line is higher than 50$\Omega$.

5. The electromagnetic receiving device of claim 4, wherein the dielectric rod has a loss factor $\varepsilon''$ such that $\varepsilon'/\varepsilon''$ exceeds about 50.

6. The electromagnetic receiving device of claim 1, wherein the dielectric rod has a loss factor $\varepsilon''$ such that $\varepsilon'/\varepsilon''$ exceeds about 50.

7. An apparatus comprising an electromagnetic transmitting device and one or more receiving devices according to at least claim 1, the apparatus being configured to collect diffracted signals from internal dielectric inhomogeneities in the object under study by using orthogonality relations between a primary magnetic field generated by the electromagnetic transmitting device, an electric field induced in the object under study by the primary magnetic field, and an electric field caused by diffraction by an internal dielectric inhomogeneity in the object under study.

8. The apparatus of claim 7, further comprising means for direct readout of the received signals as function of a receiving device position on the object under study, including means for computing, using the received signals and receiving device positions for providing a diffracted signal map over a large part of a surface of the object under study.

9. The apparatus of claim 7, wherein the permittivity of the dielectric rod is higher than an average permittivity of an outer 5 mm of the object under study, in a frequency range 1 to 5 GHz.

10. The apparatus of claim 6, in which a characteristic impedance of the coaxial line is higher than 50$\Omega$.

11. The apparatus of claim 7, wherein the dielectric rod has a loss factor $\varepsilon''$ such that $\varepsilon'/\varepsilon''$ exceeds about 50.

\* \* \* \* \*